(12) United States Patent
Tai

(10) Patent No.: US 11,051,975 B2
(45) Date of Patent: Jul. 6, 2021

(54) DEVICE AND METHOD FOR NERVE BLOCK BY LOCAL COOLING TO ROOM TEMPERATURE

(71) Applicant: University of Pittsburgh—Of the Commonwealth System of Higher Education, Pittsburgh, PA (US)

(72) Inventor: Changfeng Tai, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 302 days.

(21) Appl. No.: 15/780,748

(22) PCT Filed: Dec. 1, 2016

(86) PCT No.: PCT/US2016/064364
§ 371 (c)(1),
(2) Date: Jun. 1, 2018

(87) PCT Pub. No.: WO2017/096007
PCT Pub. Date: Jun. 8, 2017

(65) Prior Publication Data
US 2018/0344518 A1 Dec. 6, 2018

Related U.S. Application Data

(60) Provisional application No. 62/262,445, filed on Dec. 3, 2015.

(51) Int. Cl.
*A61F 7/12* (2006.01)
*A61F 7/00* (2006.01)
(Continued)

(52) U.S. Cl.
CPC .............. *A61F 7/12* (2013.01); *A61F 7/007* (2013.01); *A61F 7/02* (2013.01); *A61M 19/00* (2013.01);
(Continued)

(58) Field of Classification Search
CPC combination set(s) only.
See application file for complete search history.

(56) References Cited

U.S. PATENT DOCUMENTS

2005/0039465 A1  2/2005  Welch
2007/0135875 A1* 6/2007  Demarais ................ A61N 1/28
                                                                607/96
(Continued)

FOREIGN PATENT DOCUMENTS

JP    201418508 A    2/2014
WO    2015142838 A1  9/2015

OTHER PUBLICATIONS

Zhang et al., "Conduction block of mammalian myelinated nerve by local cooling to 15-30° C. after a brief heating", Journal of Neurophysiol, 2016, pp. 1436-1445, vol. 115.
(Continued)

*Primary Examiner* — Joseph A Stoklosa
*Assistant Examiner* — Adam J Avigan
(74) *Attorney, Agent, or Firm* — The Webb Law Firm

(57) ABSTRACT

Provided herein are methods of nerve blockage, for example for treatment of obesity, heart failure, cardiovascular disease, muscle spasms, chronic pain, or urinary retention in a patient. The method comprises first heating a nerve above physiological temperature (e.g. 37° C. in a human), such as from 43° C. to 54° C. for a duration that leads to reversible nerve blockage as opposed to nerve damage. Second, reversible nerve blockage is produced by cooling the nerve below physiological temperature to a temperature in which revers-
(Continued)

ible nerve blockage is achieved, for example from 15° C. to 30° C.

13 Claims, 9 Drawing Sheets

(51) Int. Cl.
*A61M 19/00* (2006.01)
*A61F 7/02* (2006.01)
*A61N 5/02* (2006.01)
*A61N 5/06* (2006.01)

(52) U.S. Cl.
CPC .......... *A61F 2007/0054* (2013.01); *A61F 2007/0071* (2013.01); *A61F 2007/0075* (2013.01); *A61F 2007/0086* (2013.01); *A61F 2007/0088* (2013.01); *A61F 2007/0093* (2013.01); *A61F 2007/0096* (2013.01); *A61F 2007/0285* (2013.01); *A61F 2007/0295* (2013.01); *A61F 2007/0296* (2013.01); *A61F 2007/126* (2013.01); *A61M 2205/3368* (2013.01); *A61M 2205/3523* (2013.01); *A61M 2205/3606* (2013.01); *A61M 2205/3653* (2013.01); *A61M 2205/3673* (2013.01); *A61M 2205/3686* (2013.01); *A61N 5/025* (2013.01); *A61N 5/0625* (2013.01)

(56) References Cited

U.S. PATENT DOCUMENTS

| | | | |
|---|---|---|---|
| 2007/0225781 A1* | 9/2007 | Saadat | A61F 7/12 607/105 |
| 2009/0036945 A1* | 2/2009 | Chancellor | A61N 1/36175 607/39 |
| 2009/0149926 A1 | 6/2009 | Dacey, Jr. et al. | |
| 2009/0187223 A1* | 7/2009 | Gross | A61F 7/12 607/3 |
| 2010/0222854 A1 | 9/2010 | Demarais et al. | |
| 2010/0305632 A1 | 12/2010 | Maskara et al. | |
| 2012/0310313 A1 | 12/2012 | Rogers et al. | |
| 2013/0296977 A1 | 11/2013 | Chiu et al. | |
| 2015/0051637 A1 | 2/2015 | Osorio | |
| 2017/0333708 A1* | 11/2017 | Conde | A61N 1/05 |

OTHER PUBLICATIONS

Aronov et al., "Analyzing the dynamics of brain circuits with temperature: design and implementation of a miniature thermoelectric device", J Neurosci Methods, 2011, p. 32-47, vol. 197:1.
Baylor et al., "Peripheral nerve at extreme low temperatures 2: Pharmacologic modulation of temperature effects", Cryobiology, 2009, p. 12-18, vol. 59.
Cuellar et al., "Effect of High-Frequency Alternating Current on Spinal Afferent Nociceptive Transmission", Neuromodulation, 2013, p. 318-327, vol. 16.
Floras, "Sympatheic Nervous System Activation in Human Heart Failure", Journal of the American College of Cardiology, 2009, p. 375-385, vol. 54:5.
Frankenhaeuser et al., "The Action Potential in the Myelinated Nerve Fibre of Xenopus Laevis as Computed on the Basis of Voltage Clamp Data", J. Physiol., 1964, p. 302-315, vol. 171.
Gaunt et al., "Transcutaneously Coupled, High-Frequency Electrical Stimulation of the Pudendal Nerve Blocks External Urethral Sphincter Contractions", Neurorehabilitation and Neural Repair, 2009, p. 615-626, vol. 23:6.
Hodgkin et al., "A Quantitative Description of Membrane Current and Its Application to Conduction and Excitation in Nerve", J. Physiol., 1952, p. 500-544, vol. 117.
Hoogeveen et al., "Ultrastructural changes in the rat sciatic nerve after local hyperthermia", International Journal of Hyperthermia, 1993, p. 723-730, vol. 9:5.
Imoto et al., "Use a Peltier chip with a newly devised local brain-cooling system for neocortical seizures in the rat", J Neurosurg, 2006, p. 150-156, vol. 104.
Jia et al., "Cold Nerve Injury is Enhanced by Intermittent Cooling", Muscle and Nerve, 1999, p. 1644-1652, vol. 22.
Klumpp et al., "Irreversible Differential Block of A- and C-Fibres Following Local Nerve Heating in the Cat", J.Physiol., 1980, p. 471-482, vol. 298.
Leuchtag, "Fit of the dielectric anomaly of squid axon membrane near heat-block temperature to the ferroelectric Curie-Weiss law", Biophysical Chemistry, 1995, p. 197-205, vol. 53.
Long et al., "Using temperature to analyze temporal dynamics in the songbird motor pathway", Nature, 2008, p. 189-194, vol. 456:7219.
Luzzati et al., "Structural and Electrophysiological Effects of Local Anesthetics and of Low Temperature on Myelinated Nerves: Implication of the Lipid Chains in Nerve Excitability", J. Mol. Biol., 1999, p. 1389-1402, vol. 286.
Paintal, "Block of Conduction in Mammalian Myelinated Nerve Fibres by Low Temperatures", J. Physiol., 1965, p. 1-19, vol. 180.
Rothman et al., "Local Cooling: A Therapy for Intractable Neocortical Epilepsy", Epilepsy Currents, 2003, p. 153-156, vol. 3:5.
Sarr et al., "The Empower Study: Randomized, Prospective, Double-Blind, Multicenter Trial of Vagal Blockade to Induce Weight Loss in Morbid Obesity", Obes Surg, 2012, p. 1-12, vol. 22.
Schumacher et al., "Extradural Cold Block for Selective Neurostimulation of the Bladder: Development of a New Technique", The Journal of Urology, 1999, p. 950-954, vol. 161.
Stecker et al., "Peripheral nerve at extreme low temperatures 1: Effects of Temperature on the action potential", Cryobiology, 2009, p. 1-11, vol. 59.
Tai et al., "Block of External Urethral Sphincter Contraction by High Frequency Electrical Stimulation of Pudendal Nerve", The Journal of Urology, 2004, p. 2069-2072, vol. 172.
Van Buyten et al., "High-Frequency Spinal Cord Stimulation for the Treatment of Chronic Back Pain Patients: Results of a Prospective Multicenter European Clinical Study", Neuromodulation, 2013, p. 59-66, vol. 16.
Vujaskovic et al., "Effects of intraoperative hyperthermia on peripheral nerves: Neurological and electrophysiological studies", International Journal of Hyperthermia, 1994, p. 41-49, vol. 10:1.
Waataja et al., "Effects of high-frequency alternating current on axonal conduction through the vagus nerve", Journal of Neural Engineering, 2011, p. 1-7, vol. 8.

\* cited by examiner

DEVICE AND METHOD FOR NERVE BLOCK BY LOCAL COOLING TO ROOM TEMPERATURE

CROSS-REFERENCE TO RELATED APPLICATIONS

This application is the United States national phase of International Application No. PCT/US2016/064364 filed Dec. 1, 2016, and claims the benefit of U.S. Provisional Patent Application No. 62/262,445, filed Dec. 3, 2015, each of which is incorporated herein by reference in its entirety.

STATEMENT REGARDING FEDERAL FUNDING

This invention was made with government support under Grant No. DK102427 awarded by the National Institutes of Health. The government has certain rights in the invention.

BACKGROUND OF THE INVENTION

Mammalian myelinated nerves can be blocked by locally cooling the nerves below 15° C. or by heating above 46° C. However, these extremely low or high temperatures require significant amount of energy to produce, and can also cause nerve tissue damage for a long duration application (Jia J et al. (1999). Cold nerve injury is enhanced by intermittent cooling. *Muscle & Nerve* 22, 1644-1652; Vujaskovic Z, et al., (1994). Effects of intraoperative hyperthermia on peripheral nerves: neurological and electrophysiological studies. (*Int J Hyperthermia* 10, 41-49). Therefore, clinical application of cold/heat block to treat chronic diseases currently remains to be elusive. If a thermal block of nerve conduction is practically achievable, it will have a wide range of clinical applications to treat many chronic diseases, for example, blocking the abdominal vagus nerve to treat obesity, blocking sensory axons in the dorsal roots to treat chronic pain of peripheral origin, blocking sympathetic nerves to treat heart failure, and blocking the pudendal nerve to induce efficient voiding after spinal cord injury.

Currently local anesthetic drugs are commonly used in clinical applications for nerve conduction block. Injection of local anesthetics is mainly used as an acute method for nerve block due to the difficulty in delivering these drugs in chronic applications. Recently, high-frequency (kHz) electrical stimulation generated by implantable stimulator was used clinically to block the vagus nerve for obesity treatment or block the spinal roots for chronic pain. High-frequency was also proposed to block pudendal nerve for restoring bladder function after spinal cord injury. However, the high-frequency stimulation will always generate an initial nerve firing before it can block nerve conduction. The initial nerve firing is problematic for many clinical applications such as suppressing pain, because initial painful sensation will always be induced before nerve block occurs. New methods of producing reversible nerve block are therefore desired.

SUMMARY OF THE INVENTION

As described herein, it has been discovered that mammalian myelinated nerves can be blocked by local cooling the nerve to room temperature (15° C. to 30° C.) after a brief reversible heat block. This thermal block method is safe and provides the platform to develop an implantable nerve block device to treat many chronic diseases such as obesity, pain, heart failure, and bladder dysfunction after spinal cord injury. Further, a thermal block method, as described herein, provides a reversible nerve block without generating any initial response, which provides benefits over electrical stimulation. Current thermoelectric peltier technology (Aronov D, et al., (2011). Analyzing the dynamics of brain circuits with temperature: Design and implementation of a miniature thermoelectric device. *J Neurosci Methodc* 197: 32-47; Rothman S, et al., (2003). Local cooling: A therapy for intractable neocortical epilepsy. *Epilepsy Currents* 3: 153-156) also makes it possible to design and develop an implantable device to produce a local temperature change between 15 and 50° C. Therefore, a thermal block technology as described herein has many advantages to be used for many clinical applications to treat chronic diseases such as obesity, pain, heart failure, and bladder dysfunction after spinal cord injury.

Provided herein is a method of reversibly blocking a nerve, including steps of heating the nerve to a temperature above 37° C. and below a temperature and time duration at which an irreversible nerve block is produced, and cooling the nerve to a temperature below 37° C. and above a temperature at which an irreversible nerve block is produced to produce a reversible nerve block. In aspects, the nerve is heated to a temperature ranging from 42° C. to 54° C. In aspects, the nerve is cooled to a temperature ranging from 15° C. to 30° C.

In some aspects, the method further includes a step of prior to heating the nerve, implanting a temperature controller at the nerve to heat and cool the nerve, the temperature controller comprising a heating element, a cooling element and a temperature sensor, and the temperature controller optionally being wirelessly connected to a controller for controlling heating of the heating element, cooling of the cooling element, and monitoring temperature at the nerve by the temperature sensor. In some aspects the heating element is a resistor, thin film semiconductor, a Peltier heater, a microwave radiator, or infrared heater, and the cooling element is a coolant tube, a Peltier cooler, and/or the temperature sensor is a thermocouple or a thermistor.

Also provided herein is a method of treating obesity in a patient by blocking an abdominal vagus nerve of the patient by the method described above.

Also provided herein is a method of treating heart failure in a patient by blocking a sympathetic nerve, optionally one or more of the greater splanchnic nerve, lesser splanchnic nerve, or sympathetic trunks, of the patient by the method described above.

Further provided herein is a method of treating urinary retention in a patient by blocking a pudendal nerve of the patient by the method described above.

Provided herein is a method of treating muscle spasms in a patient by blocking a nerve innervating the muscle of the patient by the method described above.

Also provided herein is a method of treating cardiovascular disease in a patient by blocking a vagus nerve of the patient by the method described above.

In addition, provided herein is a system for reversibly blocking a nerve, the system including an implantable device and an external controller. The internal device includes a temperature controller having a processor, a thermoelectric device in communication with the temperature controller and configured to be placed in proximity to a nerve, a temperature sensor in communication with the temperature controller and configured to be placed in proximity to the nerve, and a power source to provide power to the temperature controller and the thermoelectric device.

The temperature controller also has memory having stored thereon programming instructions that, when executed by the processor, cause the processor to control the thermoelectric device to heat the nerve to a temperature above 37° C. and below a temperature and time duration at which an irreversible nerve block is produced and cool the nerve to a temperature below 37° C. and above a temperature at which an irreversible nerve block is produced to produce a reversible nerve block. The external controller of the system is in communication with the temperature controller.

In some aspects, the programming instructions, when executed by the processor, further cause the processor to receive temperature information from the temperature sensor and, based on the temperature information, modify control of the thermoelectric device.

In some aspects the temperature sensor is a thermistor. In other aspects, the temperature sensors is a thermocouple.

In some aspects of the system, the thermoelectric device includes a heating element and a cooling element. In some aspects the heating element is a resistor, thin film semiconductor, a Peltier heater, a microwave radiator, or infrared heater. In some aspects the cooling element is a coolant tube or a Peltier cooler.

Further provided herein is a use of an implantable device for reversibly blocking a nerve. The implantable device includes a temperature controller having a processor, a thermoelectric device in communication with the temperature controller and configured to be placed in proximity to a nerve, a temperature sensor in communication with the temperature controller and configured to be placed in proximity to the nerve, and a power source to provide power to the temperature controller and the thermoelectric device. The device is used to provide the reversible block by heating the nerve to a temperature above 37° C. and below a temperature and time duration at which an irreversible nerve block is produced and then cooling the nerve to a temperature below 37° C. and above a temperature at which an irreversible nerve block is produced to produce a reversible nerve block.

BRIEF DESCRIPTION OF THE DRAWINGS

FIG. 8A shows the threshold temperature for a complete cold block was increased from 5° C. to 15° C. when the nerve was heated at non-block temperatures (46-48° C.) for 15 minutes. FIG. 8B shows summarized results (N=7 nerves) showing that the threshold temperature for producing complete cold block increased as the heating duration increased. * indicates a significant ($p<0.05$) increase compared to the block threshold temperature before heating (one-way ANOVA).

DETAILED DESCRIPTION

Figure 1:
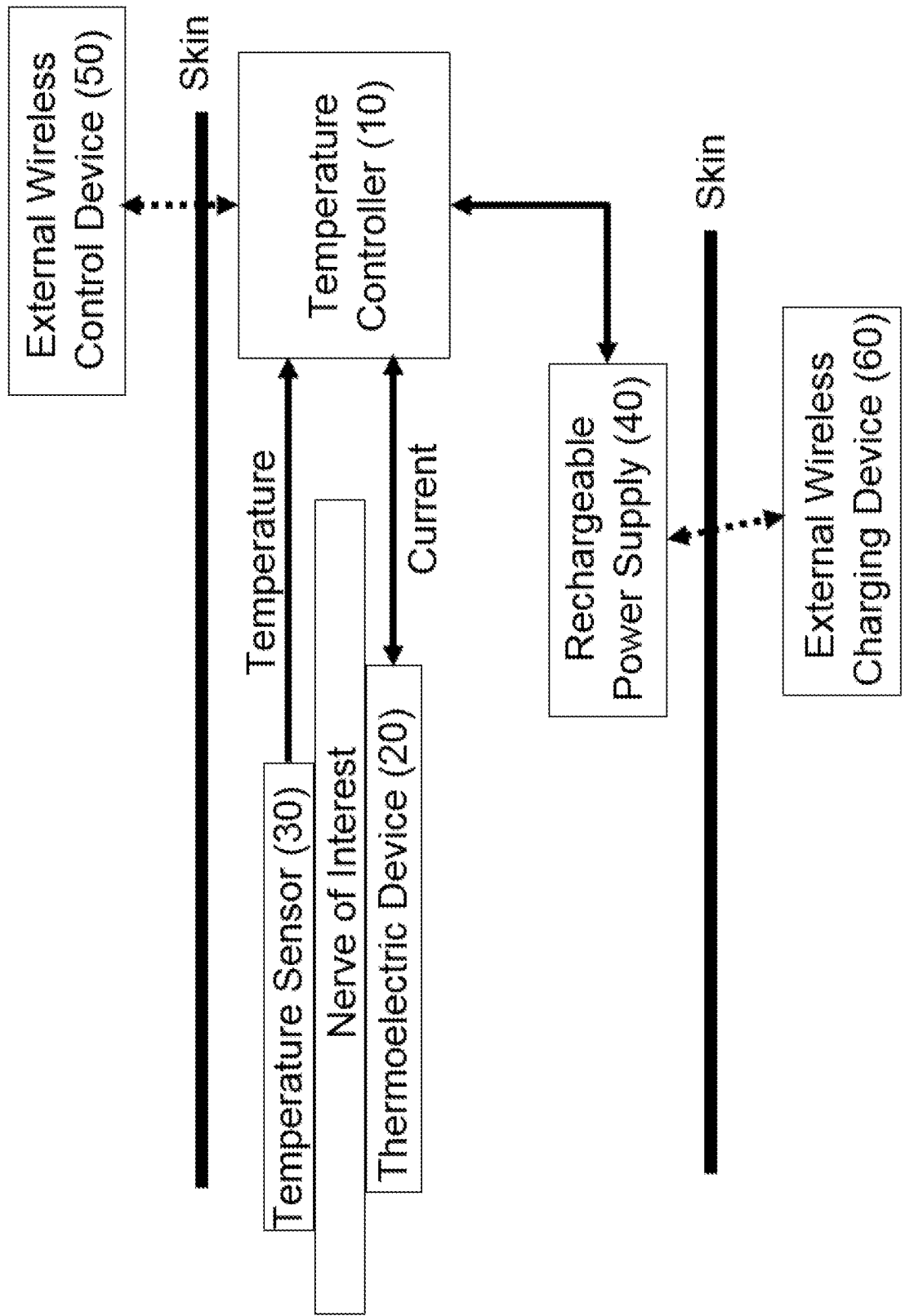
FIG. 1 shows a block diagram of a device for providing local heating and/or cooling to a nerve according to one aspect of the present invention.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

As used herein, the term "comprising" and like terms are open-ended. The term "consisting essentially of" limits the scope of a claim to the specified materials or steps and those that do not materially affect the basic and novel characteristics of the claimed invention. The term "consisting of" excludes any element, step, or ingredient not specified in the claim.

As used herein, the terms "a" and "an" refer to one or more.

As used herein, the term "patient" is any mammal, including humans, and a "human patient" is any human.

As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication can use a direct or indirect connection, and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11a/b/g/n and other radio frequency-based protocols and methods), analog transmissions, Global System for Mobile Communications (GSM), 3G/4G/LTE, BLUETOOTH, ZigBee, EnOcean, TransferJet, Wireless USB, and the like known to those of skill in the art.

A method of blocking a nerve to treat any condition in a patient, such as a human patient, treatable by such a nerve block, including, without limitation: obesity, heart failure, cardiovascular disease, chronic pain, muscle spasms, and urinary retention is provided. The method comprises heating a nerve of a patient to a temperature above physiological temperature (normal temperature for that patient, such as 37° C. for a human patient) and for a duration and time lower than a temperature and duration causing irreversible nerve block in the patient. The heating can cause reversible nerve block or no nerve block. "Nerve block" refers to rendering a nerve incapable of, or substantially incapable of, firing an action potential, propagating a nerve signal, and/or releasing a neurotransmitter. By "irreversible," in the context of a nerve block, it is meant that the nerve blockage is retained well beyond the blocking treatment (e.g., nerve damage), for example for at least one day or one week past the treatment, and by "reversible," it is meant that the nerve fully or substantially recovers from blockage either immediately or after a short period beyond the blocking period, for example within one second, minute, hour, or day, and increments there between.

The method further comprises cooling the nerve to a temperature below physiological temperature (that is, below 37° C. in a human), and above a temperature at which irreversible nerve block is achieved, e.g., 15° C. The combination of the heating and cooling of the nerve causes reversible nerve block of the nerve, and thus relief of one or more symptoms of a condition treatable by blockage of the nerve. The heating temperature ranges from 42° C. to 54° C., and for a duration that does not cause irreversible nerve block in the nerve. For example, when the nerve is heated between 50° C. and 54° C., the heating duration is less than one minute. Heating at lower temperatures, such as from 42° C. to 48° C., or from 46° C. to 48° C. for a short time, such as 60 minutes or less, 30 minutes or less, e.g., for 15 minutes, typically does not cause irreversible nerve blockage (e.g., nerve damage).

Therefore according to one aspect, a method of reversibly blocking a nerve is provided. The method comprises: heating the nerve to a temperature above 37° C. and below a temperature and time duration at which an irreversible nerve block is produced; and cooling the nerve to a temperature below 37° C. and above a temperature at which an irreversible nerve block is produced to produce a reversible nerve block. In one aspect, the nerve is heated in the heating step to a temperature ranging from 42° C. to 54° C., to a temperature ranging from 50° C. to 54° C. for a duration of less than one minute, to a temperature ranging from 43° C. to 48° C. for a duration of 60 minutes or less, or 30 minutes or less, or to a temperature and for a duration that does not cause a nerve block (a substantial or complete loss of nerve activity). In another aspect, the nerve is cooled in the cooling step to a temperature ranging from 15° C. to 30° C., for example, for a time ranging from 10 to 40 minutes. The time for the block can be extended by heating and cooling the nerve more than once, or repeatedly. In yet another aspect, the method further comprises, prior to the heating step, implanting a device at the nerve to heat and cool the nerve, the device comprising a temperature controller, a thermoelectric device including a heating element, a cooling element, and a temperature sensor.

According to one aspect, also provided is a method of treating obesity in a patient, comprising blocking an abdominal vagus nerve of the patient by a nerve block method, for example as described above According to one aspect, a method is provided of treating chronic pain in a patient, comprising blocking a nerve of the patient by a nerve block method, for example as described above.

According to another aspect, a method is provided of treating heart failure in a patient, comprising blocking a sympathetic nerve of the patient, e.g., one or more of the greater splanchnic nerve, the lesser splanchnic nerve, or the sympathetic trunks, by a nerve block method, for example as described above.

According to one aspect, a method is provided of treating cardiovascular disease in a patient, comprising blocking a vagus nerve of the patient by a nerve block method, for example as described above.

According to another aspect, a method is provided of treating urinary retention in a patient, comprising blocking a pudendal nerve of the patient by a nerve block method, for example as described above.

According to one aspect, a method is provided of treating muscle spasms in a patient, comprising blocking a nerve innervating the muscle of the patient by a nerve block method, for example as described above.

Also provided herein is a device and system for reversibly blocking a nerve by heating the nerve to a temperature above 37° C. and then cooling the nerve to a temperature ranging from 15° C. to 30° C., for example as described above. The device and system include both implantable and external components. With reference to FIG. 1, the device and system include a temperature controller (10) in communication with a thermoelectric device (20) for delivering heating and cooling to the nerve and with a temperature sensor (30). The device and system receive power from an implantable power supply (40), and receive instructions from an external controller (50).

The temperature controller (10) is in wireless communication with external controller (50). External controller (50) can have a processor, memory, and a display, such as an LCD, LED or OLED display, and an input device, such as a microphone, keypad, mouse, touchscreen, touchpad or trackpad, and the like, for entering data into the external controller (50). External controller (50) is depicted as sending and receiving wireless transmissions to temperature controller (10), to permit monitoring of one or more parameters of the temperature controller (10), thermoelectric device (20), temperature sensor (30), and/or power supply (40), including, without limitation, output signal characteristics (e.g., voltage, frequency, amplitude, etc., from the power supply to the temperature controller and to the thermoelectric device; temperature to which thermoelectric device is to be heated, temperature as measured by the temperature sensor, and/or functioning/status of any of the implanted components).

Activity of temperature controller (10) and external controller (50) is processor controlled and software/firmware installed onto the temperature controller (10) and external controller (50) hardware may be used to implement the described methods, and to provide, for example and without limitation, a GUI (graphical user interface) for the optional display associated with the external controller (50), which facilitates use of the device and system. A person of skill in the electronic arts will be able to implement such a system using readily-available electronics parts and ordinary programming skills. Proprietary chips, chipsets, etc. may be designed and manufactures to implement the devices described herein.

In one aspect, external controller (50) is a proprietary device that is specifically designed for the task, or, in another example, external controller (50) is a non-proprietary device, such as a smart phone, smart watch, tablet, portable/laptop computer, or desktop computer. As described above, communication between external controller (50) and temperature controller (10) is achieved wirelessly. Such communication can be via any suitable wireless protocol, such as near-field communication, TCP/IP (including HTTP and other protocols), WLAN (including 802.11a/b/g/n and other radio frequency-based protocols and methods), analog transmissions, Global System for Mobile Communications (GSM), 3G/4G/LTE, BLUETOOTH, ZigBee, EnOcean, TransferJet, Wireless USB, and the like known to those of skill in the art.

One potential difficulty with use of wireless devices is one of identity. An external controller (50) should only be able to control one temperature controller (10) to prevent accidental stimulation of unintended subjects, or even intentional stimulation. In its simplest form, the transmission range of the devices can also be limited to prevent transmission over distances more than a few feet, thereby limiting the chances of unintended stimulation (crosstalk). Also, any number of identity-verification mechanisms may be utilized to prevent crosstalk. In one aspect, different transmission wavelengths are used for different devices, thus lowering the likelihood of crosstalk. In another aspect, the temperature controller (10) is programmed to only respond to a transmission containing a pre-defined signal, such that the temperature controller (10) and external controller (50) must first, and/or periodically "handshake" in order to communicate. In another aspect, the temperature controller (10) and/or external controller (50) transmit encrypted signals which only can be decrypted by a key stored in the other of the temperature controller (10) and/or external controller (50). In yet another aspect, RFID tagging technology is used to ensure that the temperature controller and external controller match. Any combination of these proximity and/or identity verification measures may be used to prevent crosstalk. Other useful technologies for ensuring security and identity in communication are, or may be available and are equally applicable.

With further reference to FIG. 1, temperature controller (10) and/or external controller (50) can include memory having stored thereon programming instructions that, when executed by a processor (either included with temperature controller (10), external controller (50), or both) cause the thermoelectric device to heat or cool the nerve of interest according to the methods described herein. Such programming instructions can take into account feedback from the temperature sensor, which relays the temperature to which the nerve is heated or cooled, and, based on said feedback, to modulate output of the temperature controller to the thermoelectric device. In one aspect, the programming instructions are transferred from the external controller (50) and stored on a memory of the temperature controller (10), so that a patient need not remain near the external controller (50), for example in aspects where the external controller (50) is a desktop or laptop computer, in order for the device and system to perform the methods described herein.

Again with reference to FIG. 1, the device and system include a thermoelectric device (20) for generating heating or cooling to block the nerve of interest. Suitable thermoelectric devices include, without limitation, resistors, thin film semiconductors, Peltier heaters and coolers, microwave radiators, infrared heaters, and coolant tubes. Such devices are available commercially (e.g., Micropelt thermogeneratures and Peltier coolers commercially available from Micropelt GmbH, Freiburg Germany). In aspects of the present invention, the thermoelectric device is two or more thermoelectric devices, at least one for heating and at least one for cooling. In aspects of the present invention, the thermoelectric device (20) is one or more Peltier devices. Such devices are described in, for example, Imoto et al. (Use of a Peltier chip with a newly devised local brain-cooling system for neocortical seizures in the rat. J Neurosurg 104: 150-156, 2006) and Long and Fee (Using temperature to analyse temporal dynamics in the songbird motor pathway. Nature 456: 189-194, 2008). These devices convert electric voltage to a temperature difference. Thus, by applying differing voltages to the thermoelectric device (20), heating or cooling can be generated, and the nerve of interest is affected accordingly. The thermoelectric device (20) is in communication with the temperature controller (10), and receives power from the implantable power source (40) to generate the temperature difference and heat or cool the nerve of interest.

Again with reference to FIG. 1, the device and system include a temperature sensor (30) for detecting temperature of the nerve of interest. Suitable temperature sensors include thermocouples and thermistors. A thermocouple is a pair of conductors that form electrical connections at differing temperatures, thus producing a temperature-dependent voltage and a measure of temperature. A thermistor is a resistor, the resistance of which changes based on temperature, thus providing a measurement of temperature. The temperature sensor (30) useful in the present device and system can be a negative temperature coefficient (NTC) thermistor, in which resistance decreases as the temperature increases. Such thermistors are available commercially from, for example, Vishay Intertechnology, Inc. (Shelton, Conn.) or TE Technology, Inc. (Traverse City, Mich.). The temperature sensor (30) is in communication with the temperature controller (10) and can provide feedback to modulate the amount of energy applied to the thermoelectric device.

With further reference to FIG. 1, also included with the device and system is an implantable power supply (40). Implantable power supply (40) provides energy for temperature controller (10) and thermoelectric device (20) to generate heating/cooling of the nerve of interest. Implantable power supply (40) can be a battery, for example as are used in the pacemaker arts, for example a lithium or zinc-based battery. Implantable power supply (40) can be wirelessly rechargeable, for example and without limitation, by an external wireless charging device (60). An external wireless charging device can charge implantable power supply (40) by, for example and without limitation, inductive charging. Implantable power supply (40) can also be rechargeable through a photovoltaic array.

EXAMPLES

In this study it was shown that the temperature for producing cold block of mammalian myelinated nerves can be reversibly shifted from 5-15° C. to room temperature (15-30° C.) after a brief reversible heat block. This thermal block phenomenon raises many basic scientific questions about the influence of temperature on nerve conduction and block. More importantly, it provides the possibility to develop an implantable nerve block device to treat many chronic diseases.

Currently local anesthetic drugs are commonly used in clinical applications for nerve conduction block. Injection of local anesthetics is mainly used as an acute method for nerve block due to the difficulty in delivering these drugs in chronic applications. Recently, high-frequency (kHz) electrical stimulation generated by implantable stimulator was used clinically to block the vagus nerve for obesity treatment or block the spinal roots for chronic pain. High-frequency was also proposed to block pudendal nerve for restoring bladder function after spinal cord injury. However, the high-frequency stimulation will always generate an initial nerve firing before it can block nerve conduction. The initial nerve firing is problematic for many clinical applications such as suppressing pain, because initial painful sensation will always be induced before nerve block occurs. The thermal block method disclosed herein provides a reversible nerve block without generating any initial response. Furthermore, current thermoelectric Peltier technology also makes it possible to design and develop an implantable device to produce a local temperature change between 15° C. and 50° C. Therefore, the thermal block technology described herein has many advantages to be used for many clinical applications to treat chronic diseases such as obesity, pain, heart failure, and bladder dysfunction after spinal cord injury.

This study aimed at understanding thermal effects on nerve conduction and developing new methods to produce a reversible thermal block of axonal conduction in mammalian myelinated nerves. In 13 cats under α-chloralose anesthesia, conduction block of pudendal nerves (N=20) by cooling (5-30° C.) or heating (42-54° C.) a small segment (9 mm) of the nerve was monitored by the urethral striated muscle contractions and increases in intraurethral pressure induced by intermittent (5 sec on and 20 sec off) electrical stimulation (50 Hz, 0.2 ms) of the nerve. Cold block was observed at 5-15° C. while heat block occurred at 50-54° C. A complete cold block up to 10 minutes was fully reversible, but a complete heat block was only reversible when the heating duration was less than 1.3±0.1 minutes. A brief (<1 minute) reversible complete heat block at 50-54° C. or 15 minutes of non-block mild heating at 46-48° C. significantly increased the cold block temperature to room temperature 15-30° C. The effect of heating on cold block fully reversed within about 40 minutes. This study discovered a novel method to block mammalian myelinated nerves at room temperatures, providing the possibility to develop an implantable device to block axonal conduction and treat many chronic diseases such as obesity, pain, heart failure, and bladder dysfunction after spinal cord injury. The effect of heating on cold block is of considerable interest because it raises many basic scientific questions that may help reveal the mechanisms underlying cold or heat block of axonal conduction.

Materials and Methods

Experimental Setup

A total of 13 cats (6 female and 7 male, 3.0-4.2 kg, Liberty Research Inc., Waverly, N.Y., USA) were used in this study. The animals were anesthetized by isoflurane (2-5% in oxygen) during surgery and maintained with α-chloralose anesthesia (65 mg/kg i.v. with supplementation as needed) during data collection. A pulse oximeter (9847 V, NONIN Medical, Inc., Plymouth, Minn., USA) was attached on the tongue to monitor the heart rate and blood oxygen level. A tracheotomy was performed and a tube was inserted to maintain the airway open. A catheter was inserted into right carotid artery to monitor systemic blood pressure. Another catheter was inserted into the left cephalic vein for saline and drug administration. Through an abdominal incision, the ureters were isolated, cut and drained externally. A catheter was inserted into the urethra via a small cut in the proximal urethra. The catheter was connected to a pump and a pressure transducer via a T-connector (FIG. 2) to slowly (1 ml/min) perfuse the urethra and measure the urethral pressure increase caused by neurally evoked contractions of external urethral sphincter (EUS) striated muscle. All incisions were closed by sutures at the end of surgery.

Figure 2:
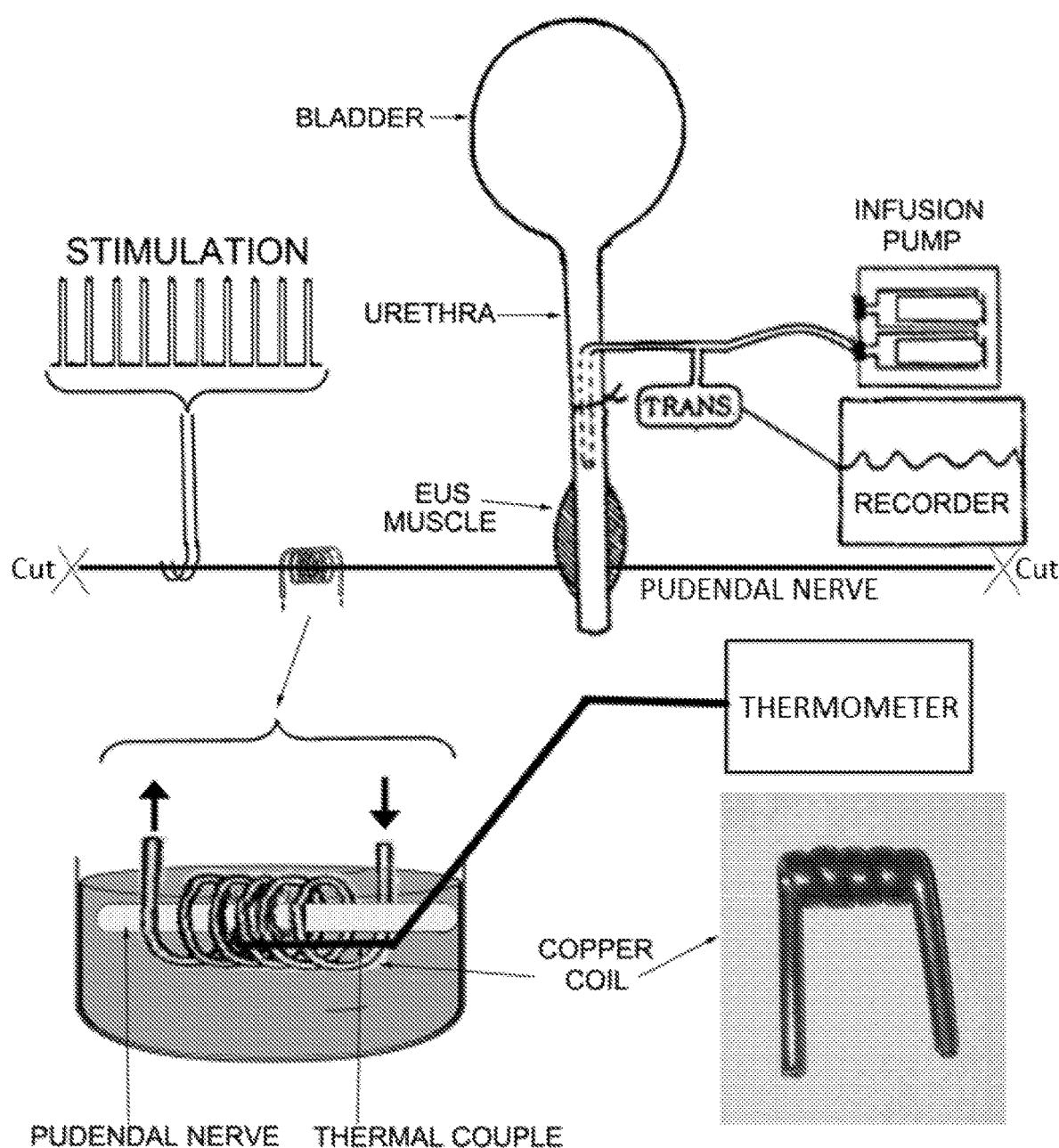
FIG. 2 shows a schematic drawing of an experimental setup for cooling a nerve to block the same according to one aspect of the present invention. A catheter was inserted into the urethra via a small cut in the proximal urethra for intraurethral infusion and pressure recording. The pudendal nerves were cut bilaterally and immersed in warm saline. One nerve was passed through a coil of copper tubing. The temperature inside the coil was changed by running water of different temperatures through the tubing. A thermocouple was placed in the middle of the copper coil to record temperature. Electrical stimulation was applied to the nerve via a hook electrode proximal to the coil to induce contractions of the external urethral sphincter (EUS) and cause increases in urethral pressure.

The pudendal nerves containing the motor axons innervating the EUS were exposed via 3-4 cm incisions between the tail and sciatic notch and cut bilaterally with the distal end tied with a suture (FIG. 2). The right or left pudendal nerve was studied individually. One of the pudendal nerves was passed through a small (9 mm long) coil (2 mm inner coil diameter) of copper tubing (FIG. 2). One end of the copper tubing (outside diameter 1.57 mm and inside diameter 0.36 mm) was connected to syringe via a plastic tube for manually infusing different temperature water to locally cool or heat the nerve segment in the coil. The temperature inside the coil was monitored by a thermometer with the thermocouple tip inserted at the center of coil (FIG. 2). The targeted temperature was maintained within ±1° C. by manually adjusting the infusion rate. A bipolar hook electrode was placed on the nerve proximal to the copper coil (FIG. 2) to test whether local temperature change inside the coil could block the urethral contraction responses induced by repeated short trains of stimulation (50 Hz, 0.2 ms, 5 secs on and 20 secs off). Stimulation intensities sufficient to generate greater than 40 cmH$_2$O increases in urethral pressure were used during the experiments. The nerve, coil, and electrodes were all immersed in the warm saline pool (35-37° C.) formed by retracting the skin flaps using sutures.

Experimental Protocol

In the first group of 9 cats, the nerve was first briefly (50-60 second duration) cooled sequentially to temperatures of 30, 25, 20, 15, 10, and 5° C. in −5° C. steps. Then, the nerve was briefly (50-60 second duration) heated sequentially to temperatures of 42, 44, 46, 48, 50, 52, and 54° C. in +2° C. steps. Between these brief cooling/heating periods, enough time (50-150 seconds) was given for the EUS contraction response to fully recover. Once a reversible complete heat block was observed (usually at 50-54° C.), the temperature was not further increased. Instead, the brief cooling protocol was repeated to examine the changes in cold block temperatures; and the duration of change was then monitored by repeatedly (50-150 interval) and briefly (50-60 seconds) cooling the nerve until the cold block temperature returned to control level. At the end of this group of experiments, different heating durations (1-3 minutes) were tested at the reversible block temperature (50-54° C.) to determine the heating duration for a non-reversible block.

In the second group of 4 cats, the repeated cooling protocol as described above was performed initially to determine the cold block temperature. Then, the nerve was heated 3 times for a period of 5 minutes to 46° C. or 48° C., which are temperatures just below the heat block temperature (50-54° C.). After each heating the cold block temperature was measured by the repeated cooling protocol.

Data Analysis

In order to measure the temperature effects on nerve conduction, the mean amplitude of the smallest urethral contraction induced by short trains of pudendal nerve stimulation during each brief cooling/heating was normalized to the mean amplitude of the urethral contraction just before the cooling/heating. The results obtained from nerves in different animals under the same experimental conditions were averaged and reported as mean±standard error. Statistical significance (p<0.05) was detected by t-test or ANOVA followed by Dunnett (one-way) or Bonferroni (two-way) multiple comparison.

Results

Conduction Block of the Pudendal Nerve by Local Cooling or Heating

Figure 3:
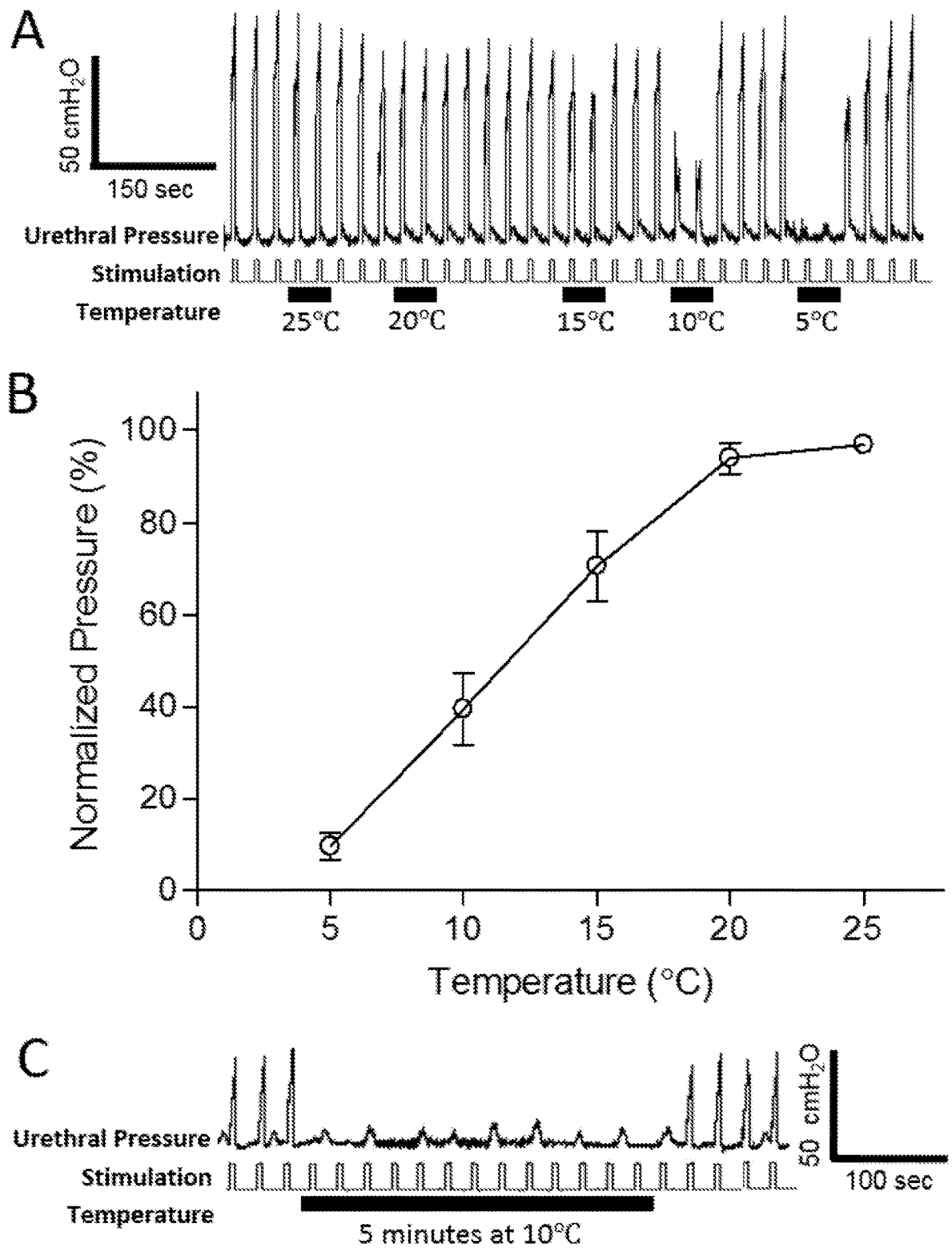
FIG. 3 shows cold block of the urethral pressure response induced by pudendal nerve stimulation (PNS). Panel A. Urethral pressure trace showing a complete nerve block at 5° C. The square wave under the trace indicates the duration of each short train (5 sec) of PNS (50 Hz, 0.2 ms, 3.2 V). The black bar under the trace indicates the duration of cooling by the copper coil. Panel B. Average urethral pressure responses at different temperatures (N=20 nerves). The mean pressure of the last response during each cooling period was normalized to the response just before the cooling. Panel C. Cold block is fully reversible even after long-lasting (5 minutes) complete block.
Figure 4:
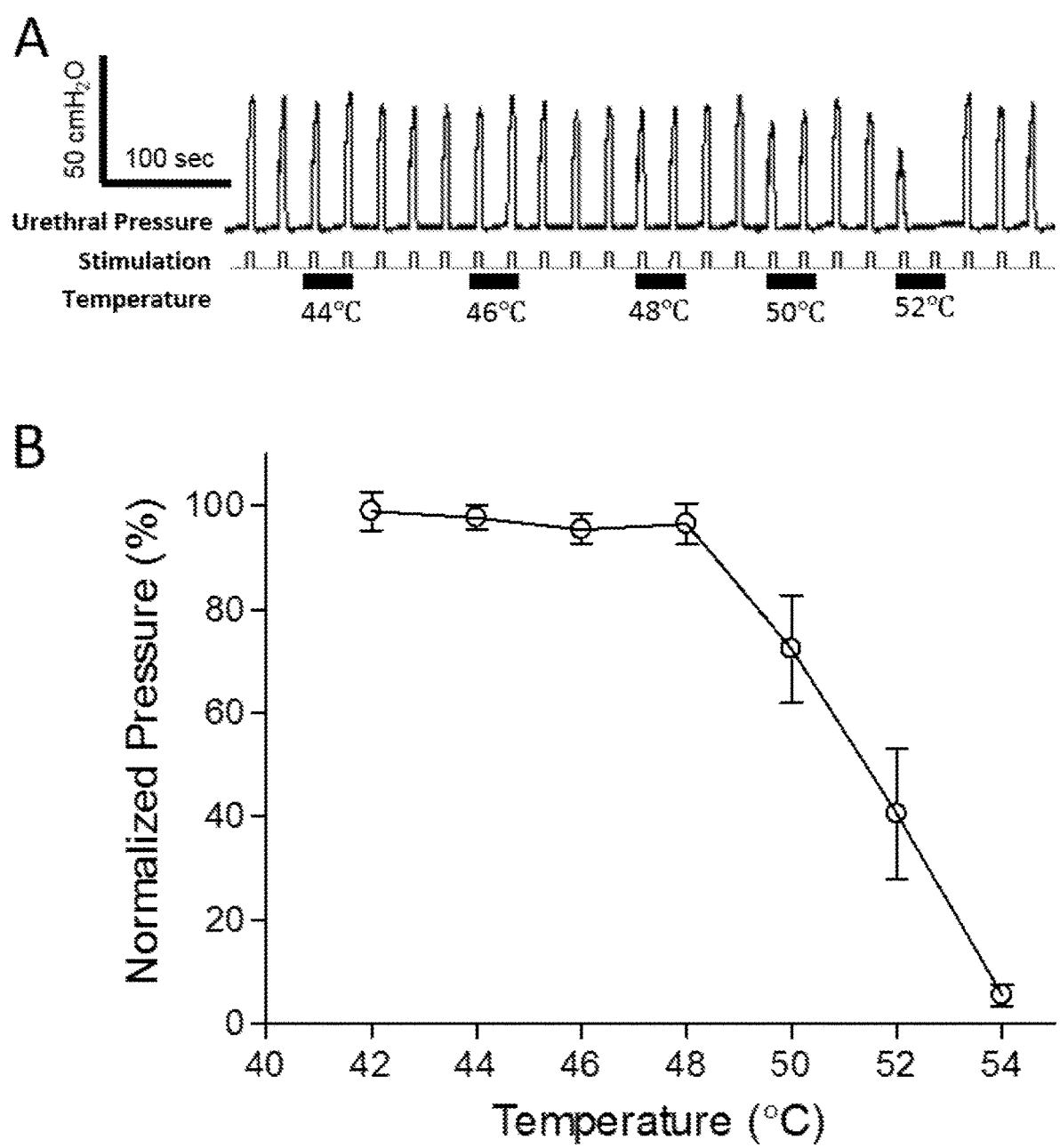
FIG. 4 shows heat block of the urethral pressure response induced by pudendal nerve stimulation (PNS). Panel A. Urethral pressure trace showing a complete nerve block at 52° C. The square wave under the trace indicates the duration of each short train (5 sec) of PNS (50 Hz, 0.2 ms, 1.0 V). The black bar under the trace indicates the duration of heating by the copper coil. Panel B. Average urethral pressure responses at different temperatures (N=14 nerves). The mean pressure of the last response during each heating period was normalized to the response just before the heating.

Short trains (5 seconds on and 20 seconds off) of pudendal nerve stimulation (50 Hz, 0.2 ms, 1-10 V) induced short duration EUS contractions that generated relatively consistent urethral pressure increases of amplitude greater than 40 cmH$_2$O (FIG. 3, panel A and FIG. 4, panel A). Manual perfusion of cold water (0-10° C.) through the copper coil quickly (5-10 seconds) reduced the temperature recorded by the thermocouple inside the coil to 5-30° C. that was maintained for 50-60 seconds (marked by the black bar under the pressure trace in FIG. 3, panel A). Once the perfusion was stopped, the temperature quickly (5-10 seconds) returned to the saline pool temperature of 35-37° C. Similarly, brief heating the nerve (FIG. 4, panel A) was achieved by manual perfusion of hot water (50-60° C.) through the copper coil.

When the temperature was gradually decreased by local cooling, a partial block of pudendal nerve conduction occurred starting at 15° C. (FIG. 3, panels A and B). In the 20 tested nerves, a complete block was achieved at 15° C. in 2 nerves, at 10° C. in 6 nerves, and at 5° C. in 8 nerves. FIG. 3, panel B shows the average results. The urethral contraction responses fully recovered once the cold temperature was returned to the warm saline pool temperature (FIG. 3, panel A), indicating that the brief (50-60 seconds) cold block was completely reversible. Long-lasting (4.5-10 minutes) complete cold block was tested in 3 nerves, showing a similar reversibility (FIG. 3, panel C).

Figure 5:
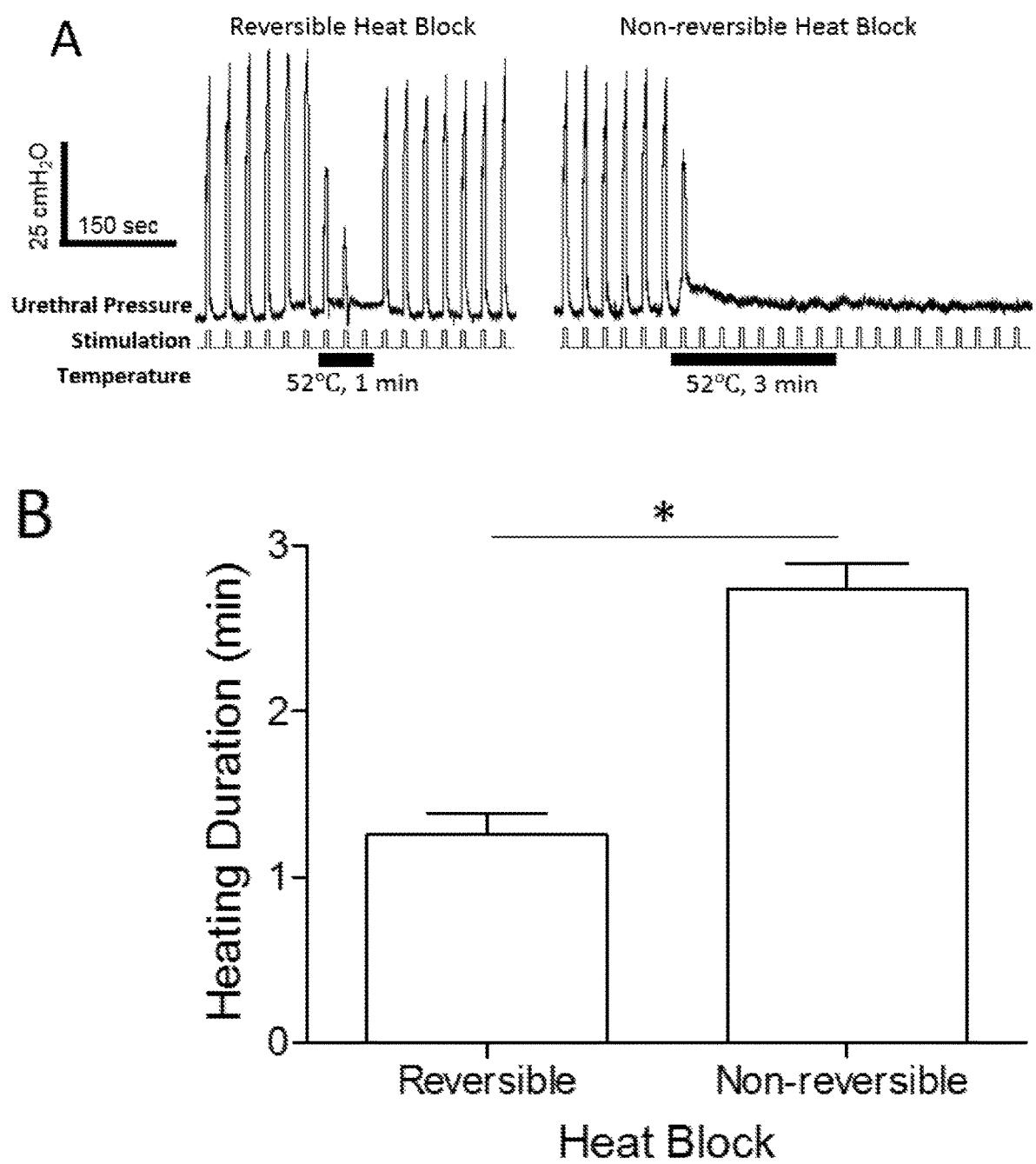
FIG. 5 shows reversibility of heat block is dependent on heating duration. Panel A. At 52° C. nerve block is reversible after 1 minute heating, but it is non-reversible after 3 minute heating. Panel B. Summarized results (N=12 nerves). Heating temperature=50-54° C. * indicates a significant difference ($p<0.0001$, paired t-test).

When the temperature was gradually increased by local heating, a partial block of nerve conduction occurred starting at 50° C. (FIG. 4, panels A and B). In the 14 tested nerves, a complete block was achieved at 50° C. in 2 nerves, at 52° C. in 6 nerves, and at 54° C. in 6 nerves. FIG. 4, panel B shows the average results. Although heat block of short duration (<1 minute) was fully reversible (FIG. 4, panel A and FIG. 5, panel A), a longer duration (3 minute) produced a partial non-reversible block or a complete loss of urethral contractions (FIG. 5, panel A). On average, reversible heat block was achieved with a heating duration of 1.3±0.1 minutes while non-reversible (partial or complete) heat block occurred with a heating duration of 2.7±0.2 minutes (FIG. 5, panel B). The non-reversible heat block (FIG. 4, panel A) was monitored for 5-45 minutes (average 17±4 minutes) in 12 nerves with no recovery of urethral contractions.

Local Heating Shifted Cold Block Temperature to 15-30° C.

Figure 6:
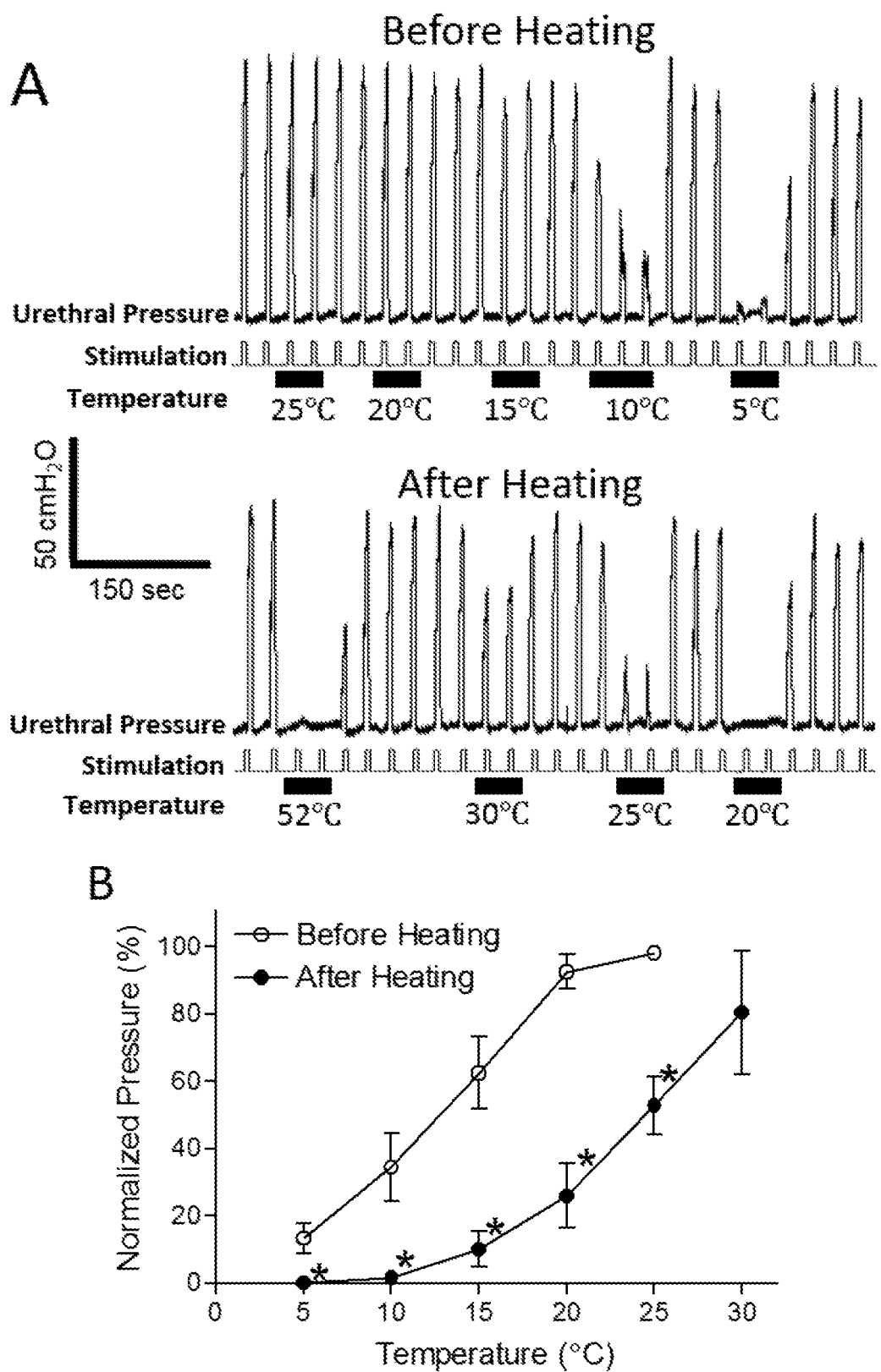
FIG. 6 shows reversible heat block increased the temperature for producing cold block. Panel A. On the same nerve, 5° C. was required for a complete cold block before heating. However, after brief reversible heat block at 52° C. complete cold block occurred at 20° C. Panel B. Summarized results (N=12 nerves) showing the cold block response curve was shifted about 10° C. to the higher temperature. Reversible heat block at 50-54° C. was applied for 0.5-1.5 minutes. * indicates a significant ($p<0.05$) difference at each temperature before and after heating (two-way ANOVA).
Figure 7:
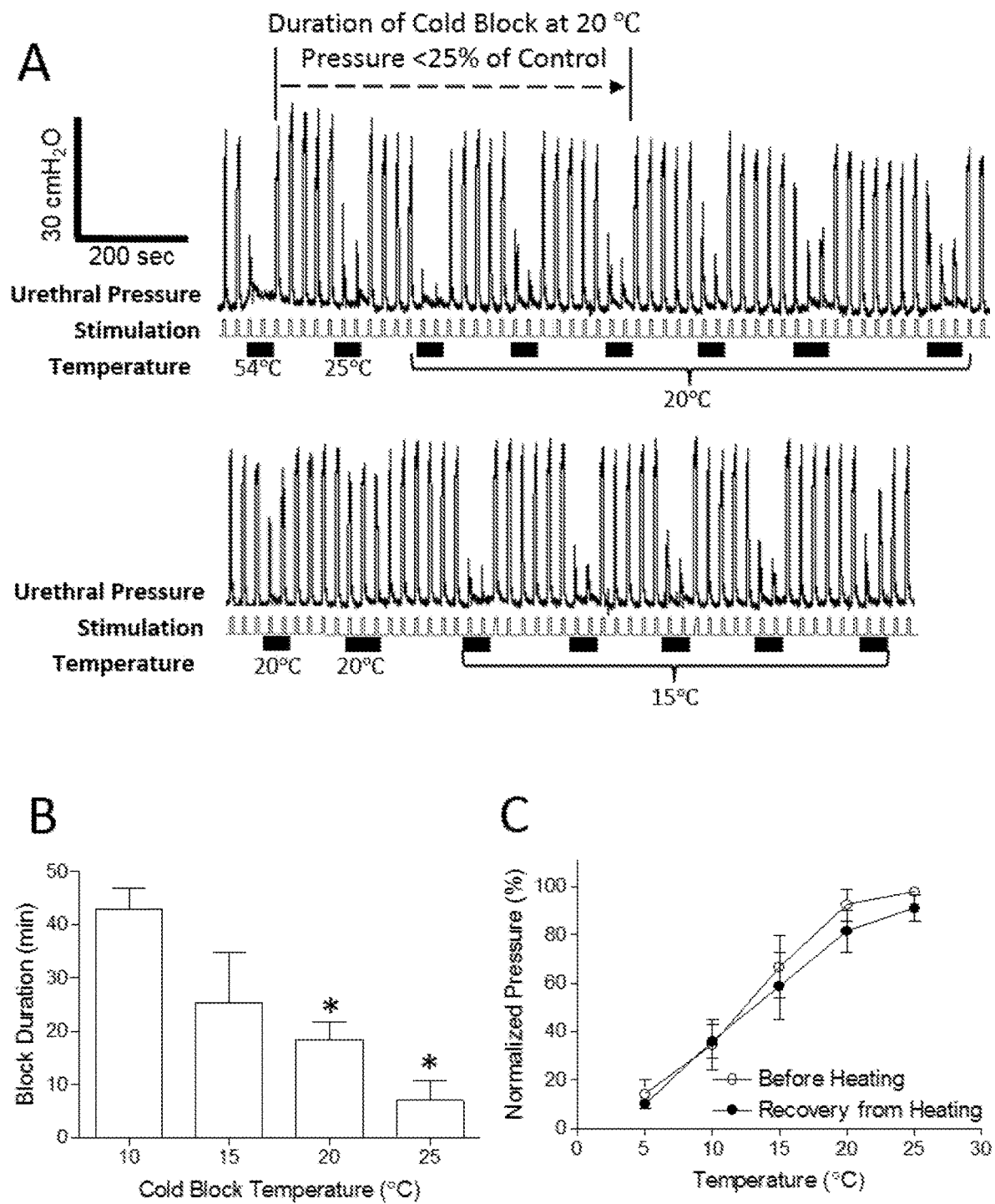
FIG. 7 shows that after a brief reversible heat block the increased temperature for cold block recovers with time. Panel A. After a brief heat block at 54° C., the cold block at 20° C. was gradually lost with time and eventually became ineffective to block nerve conduction. However, cold block at 15° C. could be achieved for a longer period than 20° C. The second trace continues from the first trace in the same animal. Panel B. The durations of cold block were different for different increased cold block temperatures. * indicates significantly ($p<0.05$) different from 10° C. data (one-way ANOVA). (N=7 nerves) Panel C. The cold block temperature curve fully recovered with time after a brief reversible heat block. Reversible heat block at 50-54° C. was applied for 0.5-1.5 minutes. (N=9 nerves)

Reversible complete heat block increased the temperature for cold block. Before any heating, a partial cold block usually occurred at 15° C. with a complete cold block at 5° C. (FIG. 6, panel A). However, after a brief (50 seconds) reversible complete heat block at 52° C. the cold block occurred on the same nerve with a partial block starting from 30° C. and a complete block at 20° C. (FIG. 6, panel A). On average a brief (0.5-1.5 minute) reversible complete heat block at 50-54° C. shifted the cold block response curve to a temperature about 10° C. higher than the control curve (FIG. 6, panel B). The duration of cold block at an increased temperature is defined as the time when the mean pressure of the smallest urethral contraction during a cold block was maintained at <25% of control (FIG. 7, panel A). The cold block at a low (15° C.) temperature lasted for a longer time than the cold block at a high (20° C.) temperature (FIG. 7, panel A). The average cold block durations at different increased temperatures are shown in FIG. 7, panel B. The increased temperature for cold block fully recovered (FIG. 7, panel B) within about 40 minutes.

Figure 8A:
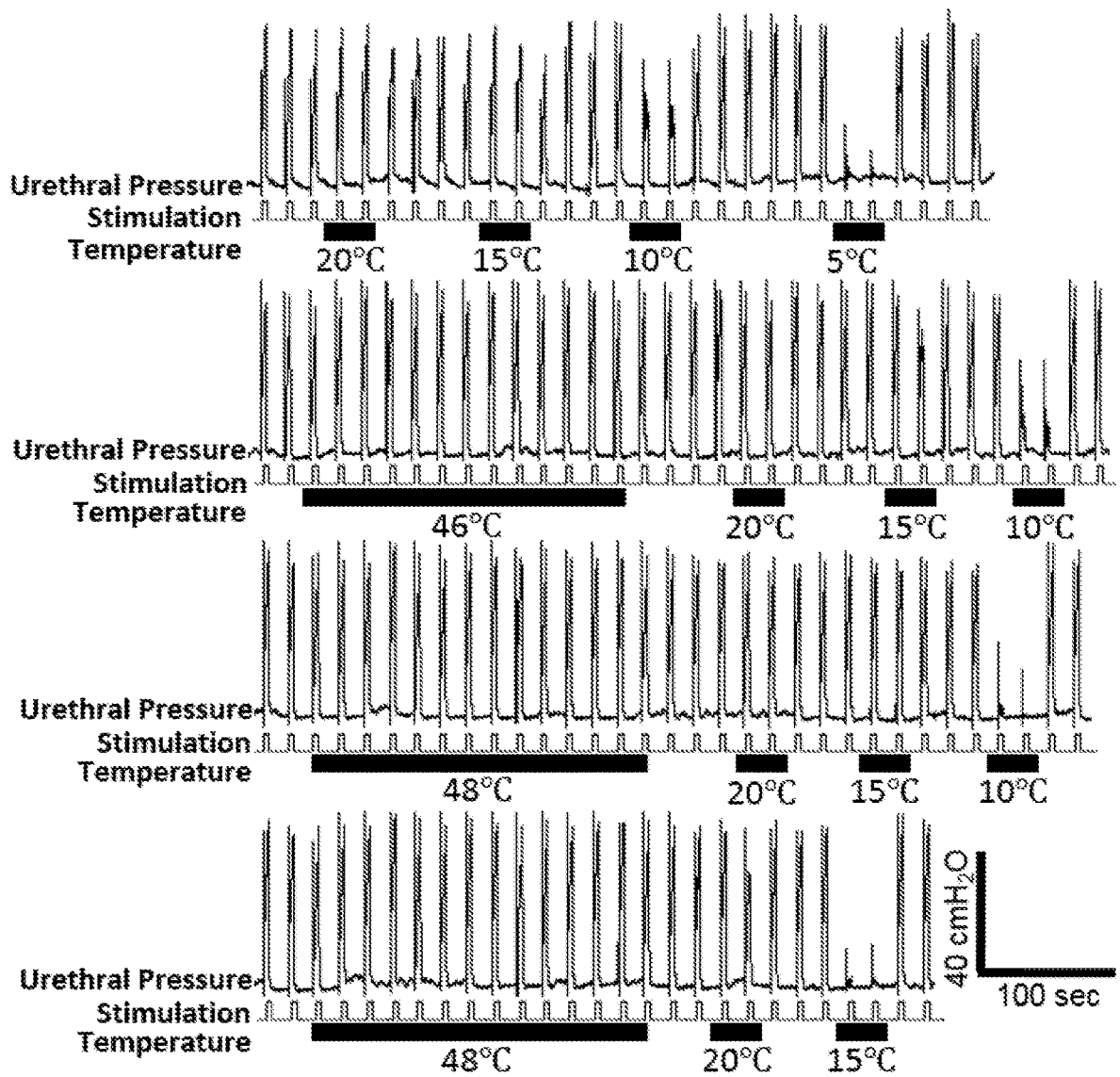
FIGS. 8A and 8B show increasing cold block temperature by non-block heating.
Figure 8B:
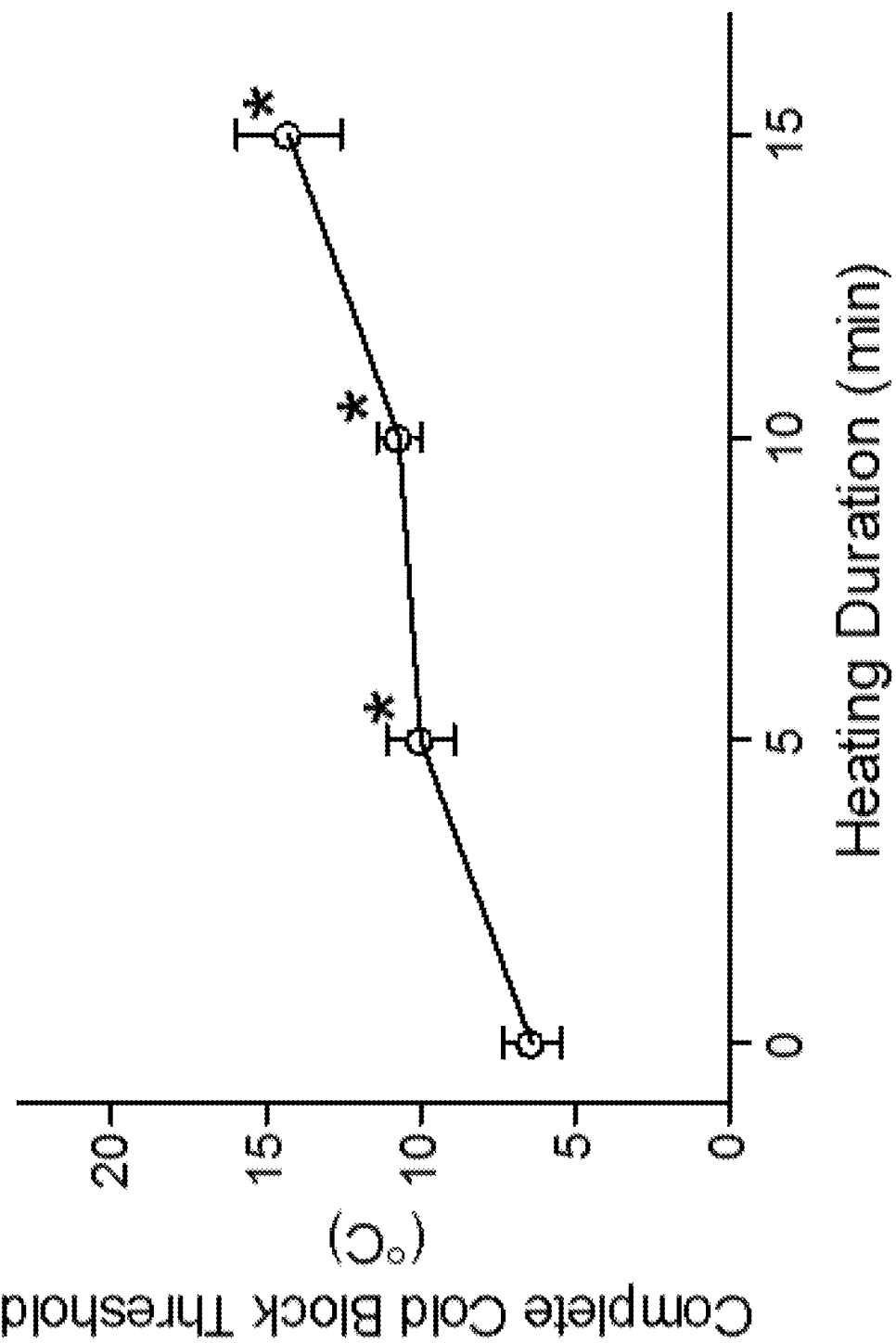

The temperature for cold block could also be increased by non-block heating at 46-48° C. Before any heating, 5° C. was usually required in order to achieve a complete nerve block (see 1st trace in FIG. 8A). However, in the same nerve repeated (3 times) heating at 46-48° C. for 5 minutes each time, which had no effect on neurally evoked urethral pressure responses, gradually increased the temperature for cold block to 15° C. (see FIG. 8A). FIG. 8B shows the average results from 7 tested nerves.

Discussion

This study in cats showed that a mammalian myelinated nerve (pudendal nerve) can be reversibly blocked by locally cooling the nerve below 15° C. for 1-10 minutes (FIG. 3) or by a brief (<1 minute) local heating above 50° C. (FIG. 4). However, the cold block temperature could be increased to room temperature 15-30° C. after a reversible complete heat block at 50-54° C. (FIG. 6) or after repeated non-block heating at 46-48° C. (FIGS. 8A and 8B). The increased temperature for cold block fully recovered with time (FIG. 7). The interaction between heating and cooling on nerve conduction is a significant observation.

It is well known that extreme cold (<15° C.) or heat (>46° C.) can block conduction in mammalian myelinated nerves. However, long-duration application of these extremely low or high temperatures can result in nerve injury. Non-reversible nerve block was produced in cats by locally heating the tibial nerve to 46.5° C. for 110 minutes or to 51° C. for 10 minutes. Although conduction block was not observed in cat tibial nerves below 46° C., it was reported in dogs that locally heating the sciatic nerve at 45° C. for 60 minutes caused a decrease in nerve conduction velocity and hindlimb dragging for 3-11 months. Nerve injury was also reported in rats when the sciatic nerve was cooled to 5° C. for 120 minutes. Therefore, it is obvious that these extremely low or high temperatures are not safe for a long duration application. However, these results showed that a very different approach can be used to achieve nerve conduction block by locally changing the nerve temperature. It only requires a brief (<1 minute) fully reversible heat block at 50-54° C. (FIG. 6) or about 15 minutes of non-block heating at 46-48° C. (FIGS. 8A and 8B) followed by a mild cooling to a room temperature (15-30° C.) to block the nerve conduction for 5-40 minutes (FIG. 7). Room temperature is probably safe for mammalian myelinated nerves. The heating durations used in this study are also probably safe because they produced fully reversible nerve block (FIG. 6) or had no effect on nerve conduction (FIGS. 8A and 8B). In addition, these heating durations are only about 10% of the durations required to produce a non-reversible nerve block. However, the safety for repeated application of the short duration heating will still need to be determined.

The cumulative effect of repeated heating on the threshold for cold block is likely dependent on the frequency of application. For clinical applications requiring very frequent applications, the effect of non-block heating at 46-48° C. could be additive and reach an unsafe level. Therefore, it is possible that temperatures below 46° C. might be used chronically to maintain the effect of non-block heating on cold block. Previous studies in rats and dogs showed that locally heating the sciatic nerve at 43-44° C. for 30-60 minutes was safe, and only produced reversible ultrastructural and electrophysiological changes on the nerve. Therefore, it is reasonable to propose a new method to block mammalian myelinated nerves by alternately applying local heating and cooling between 45° C. and 15° C. after the cold block temperature threshold has been increased by the method used in this study.

Currently other methods are used in clinical applications for nerve conduction block. Injection of local anesthetics has been used for many years to produce brief nerve block because it is difficult to deliver these drugs chronically. Recently, high-frequency (kHz) electrical stimulation generated by implantable stimulators is being used clinically to chronically block the vagus nerve for obesity treatment or to block the spinal roots for treatments of chronic pain. High-frequency stimulation has also been proposed to block the pudendal nerve to restore lower urinary tract function after spinal cord injury. However, high-frequency stimulation will always generate an initial nerve firing before it can block nerve conduction. The initial nerve firing is problematic for many clinical applications such as suppressing pain, because initial painful sensation could be induced before nerve block occurs. The thermal block method proposed in this study provides a reversible nerve block without generating an initial response. Furthermore, current thermoelectric Peltier technology also makes it possible to design and develop an implantable device to produce a local temperature change between 15 and 50° C. Therefore, a thermal block technology based on this study could potentially be used for many clinical applications to treat chronic diseases such as obesity, pain, heart failure, and bladder dysfunction after spinal cord injury.

The mechanisms underlying cold or heat block are currently unclear. However, it is well known that temperature determines the kinetics of sodium and potassium channel activity. Therefore, it is possible that extreme cold or hot temperatures can produce significant changes in ion channel kinetics to cause conduction block. However, a recent study in rats showed that the reduction in conduction velocity by cooling the sciatic nerve was not affected by a dose-dependent blockade of sodium or potassium channel, implying that the low temperature effect on conduction velocity may be related to changes in the passive properties of the myelinated axon. It is known that low temperature can thicken the axon membranes of toad sciatic nerve and reduce conduction velocity. On the other hand, the low temperature effect on the amplitude of the action potential is sensitive to a dose-dependent blockade of sodium channels. Therefore, both the ion channel kinetics and the passive properties of myelinated axons might play a role in cold block of myelinated nerve.

It is easy to understand how prolonged heat block can cause nerve damage, because it is known that excessive heating can cause edema, blood vessel occlusion, severe endothelial cell damage, and de-myelination. However, little is known about the mechanisms underlying reversible heat block. Based on what happens in cold block, it is possible that both the ion channel kinetics and the passive properties of myelinated axons could also play a role in reversible heat block. Furthermore, it is known that axonal membrane capacitance significantly increases at the heat block temperature. This locally increased capacitance can cause redistribution of charges along the axon and produce a local depolarization that may block axonal conduction.

In this study it was shown that a brief or mild heating could increase the cold block temperature (FIG. 6 and FIGS. 8A and 8B). This effect of heating on cold block can last for many minutes and is fully reversible (FIG. 7). Since ion channel kinetics change instantly with changes in temperature, they are less likely to contribute to the prolonged heating effect on cold block. However, it is possible that a brief or mild heating can cause a change in the passive properties of myelinated axons, which is fully reversible with time. More studies are contemplated to further understand the mechanisms of axonal block induced by temperature change and the interactions between cold and hot temperatures in the conduction or block of myelinated axon.

The results in this study regarding non-reversible nerve block agree well with previous studies. Cold block of sciatic nerve conduction was reported previously to occur at 5-15° C. in cats. Cold block of pudendal nerve conduction was also observed at 2-10° C. in dogs. In this study the temperature was lowered quickly (within 5-10 seconds) and then maintained for only 50-60 seconds. A previous study of rat sciatic nerve used a much slower cooling protocol by lowering the temperature at a rate of about 0.1° C./min, which corresponds to a duration of about 20 minutes for each temperature (±1° C.) tested in this study. Even with such a slow temperature change a temperature below 16° C. was still required to block the conduction of sciatic nerve in rats, indicating that the cooling protocol used in this study is accurate enough to determine the cold block response curve (FIG. 3, panel B). It is worth noting that cold block occurs in a wider temperature range (5-15° C.) than heat block (50-54° C.), which may indicate very different mechanisms for cold and heat block. In addition, it is known that cold block temperature is not related to nerve conduction velocity. Therefore, the gradual block as the temperature becomes lower (FIG. 3) is more likely due to the temperature gradient in the nerve generated by the cooper coil rather than due to blocking axons of different diameters.

A previous study in cats reported that a temperature greater than 46° C. was required for a heat block of myelinated axons. This temperature for heat block that is slightly lower than the threshold blocking temperature in this study (FIG. 4) could reflect different experimental methods. The length of the heated nerve was 15 mm in the previous study, but was only 9 mm in this study. The effect of heating or cooling different lengths of nerve might be investigated. The duration of the increased sensitivity to cold block might also be prolonged with additional intermittent mild heating at 42-44° C.

In summary, the prolonged effect of a brief period of heating on the threshold temperature for producing cold block of axonal conduction is an important observation that will lead to new insights into the physiological properties of myelinated axons and to the development of new clinical methods to treat neurogenic dysfunctions using thermal-induced changes in axonal conduction.

Having described this invention, it will be understood to those of ordinary skill in the art that the same can be performed within a wide and equivalent range of conditions, formulations and other parameters without affecting the scope of the invention or any embodiment thereof.

The following clauses are illustrative of various aspects of the invention:

Clause 1: A method of reversibly blocking a nerve, comprising:
 a. heating the nerve to a temperature above 37° C. and below a temperature and time duration at which an irreversible nerve block is produced; and
 b. cooling the nerve to a temperature below 37° C. and above a temperature at which an irreversible nerve block is produced to produce a reversible nerve block.

Clause 2: The method of clause 1, in which the nerve is heated in step a. to a temperature ranging from 42° C. to 54° C.

Clause 3: The method of clause 1 or clause 2, in which the nerve is heated in step a. to a temperature ranging from 50° C. to 54° C. for a duration of less than one minute.

Clause 4: The method of clause 1 or clause 2, in which the nerve is heated in step a. to a temperature ranging from 43° C. to 48° C. for a duration of 60 minutes or less, or 30 minutes or less.

Clause 5: The method of any of clauses 1-4, in which the nerve is heated in step a. to a temperature and for a duration that does or does not cause a nerve block.

Clause 6: The method of any of clauses 1-5, in which the nerve is cooled in step b. to a temperature ranging from 15° C. to 30° C.

Clause 7: The method of any of clauses 1-6, further comprising, prior to step a., implanting a temperature controller at the nerve to heat and cool the nerve, the temperature controller comprising a heating element, a cooling element and a temperature sensor.

Clause 8: The method of clause 7, in which the temperature controller is connected, e.g., electrically or wirelessly to a controller for controlling heating of the heating element, cooling of the cooling element, and monitoring temperature at the nerve by the temperature sensor.

Clause 9: The method of any of clauses 7 or 8, wherein the heating element is a resistor, thin film semiconductor, a Peltier heater, a microwave radiator, or infrared heater, the cooling element is a coolant tube, a Peltier cooler, and/or the temperature sensor is a thermocouple or a thermistor.

Clause 10: A method of treating obesity in a patient, comprising blocking an abdominal vagus nerve of the patient by a method of any one of clauses 1-9.

Clause 11: A method of treating chronic pain in a patient, comprising blocking a nerve of the patient by a method of any one of clauses 1-9.

Clause 12: A method of treating heart failure in a patient, comprising blocking a sympathetic nerve of the patient by a method of any one of clauses 1-9.

Clause 13: The method of clause 12, in which the sympathetic nerve is one or more of the greater splanchnic nerve, lesser splanchnic nerve, or sympathetic trunks.

Clause 14: A method of treating urinary retention in a patient, comprising blocking a pudendal nerve of the patient by a method of any one of clauses 1-9.

Clause 15: A method of treating muscle spasms in a patient, comprising blocking a nerve innervating the muscle of the patient by a method of any one of clauses 1-9.

Clause 16: A method of treating cardiovascular disease in a patient, comprising blocking a vagus nerve of the patient by a method of any one of clauses 1-9.

Clause 17: A system for reversibly blocking a nerve, comprising:
 an implantable device comprising:
  a temperature controller comprising a processor;
  a thermoelectric device in communication with the temperature controller and configured to be place in proximity to a nerve;
  a temperature sensor in communication with the temperature controller and configured to be placed in proximity to the nerve; and
  a power source to provide power to the temperature controller and the thermoelectric device; and
 an external controller in communication with the temperature controller,
 wherein the temperature controller comprises memory having stored thereon programming instructions that, when executed by the processor, cause the processor to control the thermoelectric device to:
  heat the nerve to a temperature above 37° C. and below a temperature and time duration at which an irreversible nerve block is produced; and
  cool the nerve to a temperature below 37° C. and above a temperature at which an irreversible nerve block is produced to produce a reversible nerve block.

Clause 18: The system of clause 17, wherein the programming instructions, when executed by the processor, further cause the processor to receive temperature information from the temperature sensor and, based on the temperature information, modify control of the thermoelectric device.

Clause 19: The system of clause 17 or clause 18, wherein the temperature sensor is a thermistor.

Clause 20: The system of any of clauses 17-19, wherein the temperature sensor is a thermocouple.

Clause 21: The system of any of clauses 17-20, wherein the thermoelectric device comprises a heating element and a cooling element, and wherein the heating element is a resistor, thin film semiconductor, a Peltier heater, a microwave radiator, or infrared heater, and the cooling element is a coolant tube or a Peltier cooler.

Clause 22: The system of any of clauses 17-21, wherein the power source is a rechargeable battery.

Clause 23: The system of clause 22, wherein the rechargeable battery is wirelessly rechargeable.

Clause 24: The system of clause 23, wherein the battery is configured to be recharged by induction.

Clause 25: The system of any of clauses 17-24, wherein the external controller communicates wirelessly with the temperature controller.

Clause 26: The system of any of clauses 17-25, wherein the external controller is a mobile phone, tablet, smart watch, laptop computer, or desktop computer.

Clause 27: Use of an implantable device comprising:
- a temperature controller comprising a processor;
- a thermoelectric device in communication with the temperature controller and configured to be place in proximity to a nerve;
- a temperature sensor in communication with the temperature controller and configured to be placed in proximity to the nerve; and
- a power source to provide power to the temperature controller and the thermoelectric device for reversibly blocking the nerve, comprising heating the nerve to a temperature above 37° C. and below a temperature and time duration at which an irreversible nerve block is produced; and then cooling the nerve to a temperature below 37° C. and above a temperature at which an irreversible nerve block is produced to produce a reversible nerve block.

What is claimed is:

1. A method of reversibly blocking a nerve, comprising:
   first heating the nerve to a temperature above ranging from 42° C. to 54° C. for a time period sufficient to increase the threshold temperature for producing a cold conduction block within the nerve and below a temperature and time duration at which an irreversible nerve block is produced; and
   then cooling the nerve to a temperature ranging from 15° C. to 30° C. to produce a reversible nerve block at a higher temperature than would be required without the heating step.

2. The method of claim 1, further comprising, prior to heating the nerve, implanting a temperature controller at the nerve to heat and cool the nerve, the temperature controller comprising a heating element, a cooling element and a temperature sensor, and the temperature controller optionally being wirelessly connected to a controller for controlling heating of the heating element, cooling of the cooling element, and monitoring temperature at the nerve by the temperature sensor.

3. The method of claim 2, wherein the heating element is a resistor, thin film semiconductor, a Peltier heater, a microwave radiator, or infrared heater, the cooling element is a coolant tube, a Peltier cooler, and/or the temperature sensor is a thermocouple or a thermistor.

4. The method of claim 1, for treating obesity in a patient, wherein the nerve is an abdominal vagus nerve of the patient.

5. The method of claim 1, for treating heart failure in a patient, wherein the nerve is a sympathetic nerve, optionally one or more of the greater splanchnic nerve, lesser splanchnic nerve, or sympathetic trunks, of the patient.

6. The method of claim 1, for treating urinary retention in a patient, wherein the nerve is a pudendal nerve of the patient.

7. The method of claim 1, for treating muscle spasms in a patient, wherein the nerve is a nerve innervating the muscle of the patient.

8. The method of claim 1, for treating cardiovascular disease in a patient, wherein the nerve is a vagus nerve of the patient.

9. A system for reversibly blocking a nerve, comprising:
   a device comprising:
   - a temperature controller comprising a processor;
   - a thermoelectric device in communication with the temperature controller and configured to be placed in proximity to a nerve;
   - a temperature sensor in communication with the temperature controller and configured to be placed in proximity to the nerve; and
   - a power source to provide power to the temperature controller and the thermoelectric device; and
   - a controller in communication with the temperature controller, wherein the temperature controller comprises memory having stored thereon programming instructions that, when executed by the processor, cause the processor to control the thermoelectric device to:
     first heat the nerve to a temperature ranging from 42° C. to 54° C. for a time period sufficient to increase the threshold temperature for producing a cold conduction block within the nerve and below a temperature and time duration at which an irreversible nerve block is produced; and
     then cool the nerve to a temperature ranging from 15° C. to 30° C. to produce a reversible nerve block at a higher temperature than would be required without the heating step.

10. The system of claim 9, wherein the programming instructions, when executed by the processor, further cause the processor to receive temperature information from the temperature sensor and, based on the temperature information, modify control of the thermoelectric device.

11. The system of claim 9, wherein the temperature sensor is a thermistor or a thermocouple.

12. The system of claim 9, wherein the thermoelectric device comprises a heating element and a cooling element, and wherein the heating element is a resistor, thin film semiconductor, a Peltier heater, a microwave radiator, or infrared heater, and the cooling element is a coolant tube or a Peltier cooler.

13. A system for reversibly blocking a nerve, comprising:
    a device comprising:
    - a temperature controller comprising a processor;
    - a thermoelectric device in communication with the temperature controller and configured to provide heating or cooling to a nerve;
    - a temperature sensor in communication with the temperature controller and configured to sense the temperature of the nerve; and
    - a power source to provide power to the temperature controller and the thermoelectric device; and
    - a controller in communication with the temperature controller, wherein the temperature controller comprises memory having stored thereon programming instructions that, when executed by the processor, cause the processor to control the thermoelectric device to:

first heat the nerve to a temperature ranging from 42° C. to 54° C. for a time period sufficient to increase the threshold temperature for producing a cold conduction block within the nerve and below a temperature and time duration at which an irreversible nerve block is produced; and then cool the nerve to a temperature ranging from 15° C. to 30° C. to produce a reversible nerve block at a higher temperature than would be required without the heating step.

* * * * *

UNITED STATES PATENT AND TRADEMARK OFFICE
CERTIFICATE OF CORRECTION

PATENT NO. : 11,051,975 B2
APPLICATION NO. : 15/780748
DATED : July 6, 2021
INVENTOR(S) : Changfeng Tai Page 1 of 1

It is certified that error appears in the above-identified patent and that said Letters Patent is hereby corrected as shown below:

In the Claims

Column 17, Line 39, Claim 1, after "temperature" delete "above"

Signed and Sealed this
Third Day of May, 2022

Katherine Kelly Vidal
Director of the United States Patent and Trademark Office